US012685673B1

(12) United States Patent
Triplett et al.

(10) Patent No.: US 12,685,673 B1
(45) Date of Patent: Jul. 21, 2026

(54) EARPLUG SYSTEM AND METHODS

(71) Applicant: Apothecary Products, LLC,
Burnsville, MN (US)

(72) Inventors: Tyson Triplett, Provo, UT (US);
Darran Spence, Burnsville, MN (US);
Laurel Weeks, Burnsville, MN (US);
Melissa Rowland, Burnsville, MN
(US); Julia Olson Augdahl, Prior Lake,
MN (US)

(73) Assignee: Apothecary Products, LLC,
Burnsville, MN (US)

( * ) Notice: Subject to any disclaimer, the term of this
patent is extended or adjusted under 35
U.S.C. 154(b) by 0 days.

(21) Appl. No.: 19/352,129

(22) Filed: Oct. 7, 2025

(51) Int. Cl.
*A61F 11/12* (2006.01)

(52) U.S. Cl.
CPC .................................. *A61F 11/12* (2013.01)

(58) Field of Classification Search
CPC A61F 11/12; A61F 11/08; A61F 11/06; A61F
11/00; A61F 11/14; A61F 11/145; A61F
11/30
See application file for complete search history.

(56) References Cited

U.S. PATENT DOCUMENTS

| | | |
|---|---|---|
| 416,287 A | 12/1889 | Bates |
| 7,715,888 B2 | 5/2010 | Ko |
| 8,311,260 B2 | 11/2012 | Miller |
| D674,769 S | 1/2013 | Zimmerman |
| 8,931,489 B2 | 1/2015 | Smith |
| 9,621,978 B2 | 4/2017 | Ushakov |
| D786,217 S | 5/2017 | Stoch |
| 9,706,283 B2 | 7/2017 | Stoch |
| 9,961,429 B2 | 5/2018 | Williams et al. |
| 10,080,075 B2 | 9/2018 | Kang et al. |
| D831,610 S | 10/2018 | Aoyagi et al. |
| 10,314,385 B2 | 6/2019 | Lim |
| 10,412,495 B2 | 9/2019 | Stitz |
| 11,388,505 B2 | 7/2022 | Wolfe |
| 11,389,332 B2 | 7/2022 | Cran |

(Continued)

FOREIGN PATENT DOCUMENTS

| | | |
|---|---|---|
| AU | 2022283677 | 6/2024 |
| CN | 204119444 U | 1/2015 |

(Continued)

OTHER PUBLICATIONS

Sood; "Earphones that magnetically hang like a necklace for the ultimate tech fashion statement," found at: https://www.yankodesign.com/author/gauray-sood/; Sep. 21, 2020, 6 pages.

*Primary Examiner* — Tarla R Patel
(74) *Attorney, Agent, or Firm* — Merchant & Gould P.C.

(57) ABSTRACT

An earplug system includes a pair of earplugs connected by a cord, with each earplug having a body that holds a magnet of opposite polarity to permit selective coupling and uncoupling. When not being used for hearing protection, the earplugs can be magnetically coupled together to form an aesthetically pleasing pendant that hangs around the user's neck via the cord. Each earplug includes a removable tip for insertion into the ear and a body constructed from compliant materials. Optional features include indexing systems for proper alignment, removable cord attachments, and passive acoustic filters for frequency-specific attenuation.

19 Claims, 8 Drawing Sheets

(56)                References Cited

U.S. PATENT DOCUMENTS

| | | | |
|---|---|---|---|
| 11,471,331 | B2 | 10/2022 | Dittrich et al. |
| 11,570,540 | B2 | 1/2023 | Honeycutt |
| 11,849,816 | B2 | 12/2023 | Fernando |
| 2014/0037102 | A1 | 2/2014 | Alanis |
| 2014/0338397 | A1 | 11/2014 | Andreini, III et al. |
| 2016/0080855 | A1 | 3/2016 | Greenberg et al. |
| 2017/0264729 | A1 | 9/2017 | Nelson |
| 2021/0051392 | A1 | 2/2021 | Green |
| 2021/0186761 | A1 | 6/2021 | Smit |

FOREIGN PATENT DOCUMENTS

| | | | | |
|---|---|---|---|---|
| CN | 204598251 | U | | 8/2015 |
| CN | 204598252 | U | | 8/2015 |
| CN | 204887357 | U | | 12/2015 |
| CN | 204948297 | U | | 1/2016 |
| CN | 205512788 | U | | 8/2016 |
| CN | 206302538 | U | | 7/2017 |
| CN | 207720365 | | | 8/2018 |
| CN | 207854109 | | | 9/2018 |
| CN | 208015940 | | | 10/2018 |
| CN | 208241839 | | | 12/2018 |
| CN | 208850004 | | | 5/2019 |
| CN | 209915188 | | | 1/2020 |
| CN | 305750721 | | | 5/2020 |
| CN | 211152170 | | | 7/2020 |
| CN | 211378230 | | | 8/2020 |
| CN | 111836172 | | | 10/2020 |
| CN | 212324345 | | | 1/2021 |
| CN | 212544011 | | | 2/2021 |
| CN | 212544011 | U | * | 2/2021 |
| CN | 215420714 | | | 1/2022 |
| CN | 220673903 | | | 3/2024 |
| EP | 2991370 | A1 | | 3/2016 |
| EP | 3107313 | | | 4/2019 |
| KR | 1020150103258 | A | | 9/2015 |
| KR | 200483250 | Y1 | | 4/2017 |
| TW | M416287 | U | | 11/2011 |
| WO | 2015113498 | A1 | | 8/2015 |
| WO | 2016197193 | A1 | | 12/2016 |

* cited by examiner

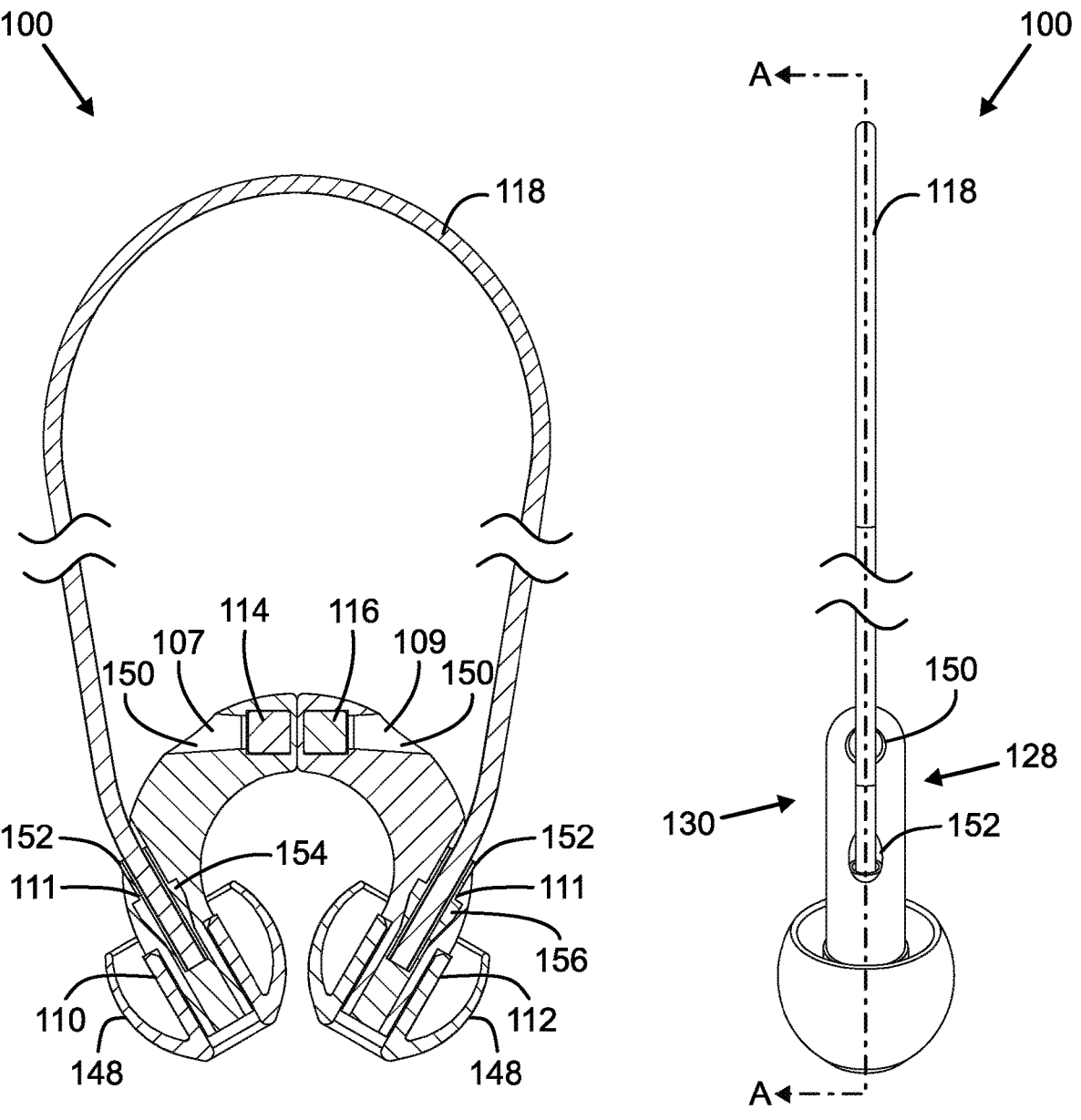
Fig. 2                                    Fig. 3

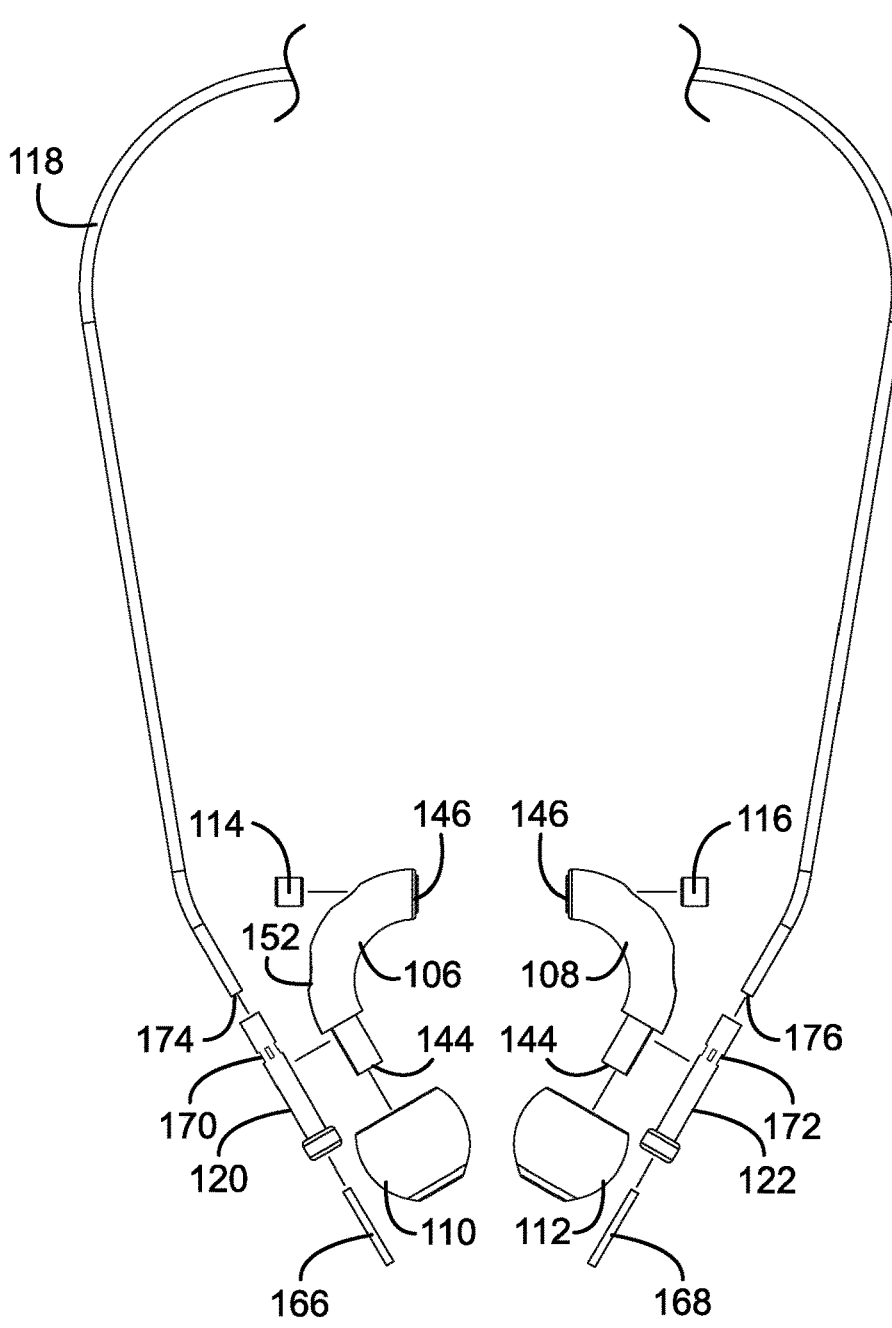
Fig. 9

EARPLUG SYSTEM AND METHODS

TECHNICAL FIELD

This disclosure relates to earplugs for hearing protection. In particular, this disclosure relates to earplugs that, in addition to being used for hearing protection, can also be worn as an aesthetically pleasing pendant, when not being used for hearing protection.

BACKGROUND

Earplugs for hearing protection are well-known. When not in use, the user needs to find a place for storage so as not to lose them. While it is also well-known to connect earplugs with a cord, to be draped around the user's neck, this appearance can be not fashionable.

What is needed is an earplug system that is effective for hearing protection, as well as convenient for storage and is aesthetically pleasing.

SUMMARY

In an aspect, an earplug system for a human is provided, the system comprising: (a) a pair of earplugs; each of the earplugs being constructed and arranged to reduce a volume of external noise for the human, when inserted into ears of the human; (b) a pair of magnets of oriented with opposing poles facing each other; each of the magnets being held by one of the earplugs to permit the earplugs to be selectively coupled and uncoupled from each other; and (c) a cord extending between the earplugs; the cord having a length between the earplugs of at least 14 inches.

In an example embodiment, each of the earplugs includes: (a) a body holding one of the magnets and being attached to the cord; and (b) a tip constructed and arranged to be insertable into the human ear, wherein the tip comprises rubber or foam and is removably attached to the body.

In some arrangements, the cord includes a pair of cord end constructions on opposite ends of the cord, with each cord end construction being attached to the body of one of the earplugs.

In example implementations, each body includes a magnet pocket holding one of the magnets and a cord-receiving cavity for the cord end construction.

In some arrangements, each one of the cord end constructions is non-removably attached to a respective one of the earplug bodies in the cord-receiving cavity.

In other arrangements, each one of the cord end constructions is removably attached to a respective one of the earplug bodies, wherein each body includes a cord slot in communication with the cord-receiving cavity to facilitate the removable attachment.

In an example embodiment, each body includes an indexing protrusion and recess arrangement to assist with alignment between the magnets.

Some arrangements may include a plurality of ribs on each body to enhance friction with one of the tips.

In example implementations, each body is shaped such that when magnetically coupled together, the bodies form a pendant having opposite front and rear surfaces each being contained within parallel planes.

The system may further include a pair of passive acoustic filters for each earplug, wherein each of the passive acoustic filters is held by a respective one of the cord end constructions.

In an example embodiment, each body comprises silicone or urethane rubber; each of the magnets comprises neodymium embedded or insert-molded into one of the bodies; each cord end construction comprises rigid plastic; and each cord comprises one of tubing, filament, or braided fiber.

In another aspect, a method of using an earplug system is provided, the method comprising: (a) removing an earplug from each ear of a user; each earplug having a body holding a magnet, a tip removably attached to the body, and a cord secured to the body and securing the earplugs to each other; (b) magnetically coupling the earplugs to each other to form a pendant; and (c) allowing the pendant to hang from a neck of the user, with the cord extending around the neck of the user.

Some methods include wherein the step of removing the earplug from each ear includes pulling on the cord to remove the tip of each earplug from one of the ears.

In some methods, the step of magnetically coupling the earplugs includes inserting a first projection from a first of the earplugs into a second recess of a second of the earplugs, and inserting a second projection from the second of the earplugs into a first recess of the first earplug.

In example implementations, the step of magnetically coupling the earplugs forms a pendant having opposite front and rear surfaces each being contained within parallel planes.

The method may further include removing the cord from the earplugs, and providing a different cord and removably attaching the different cord to the bodies of the earplugs.

Some methods further include, before the step of removing the earplug from each ear of a user, filtering out sound using a passive acoustic filter in each earplug.

Features and advantages disclosed for one of the above aspects of the present disclosure are hereby also implicitly disclosed for the other aspects, mutatis mutandis, as the skilled person will recognize.

BRIEF DESCRIPTION OF THE DRAWINGS

FIG. 2 is a cross-sectional view of the earplug system of FIG. 1, the cross-section being taken along the line A-A of FIG. 3.

FIG. 3 is a side elevational view of the earplug system of FIG. 1.

Figures 5, 6:
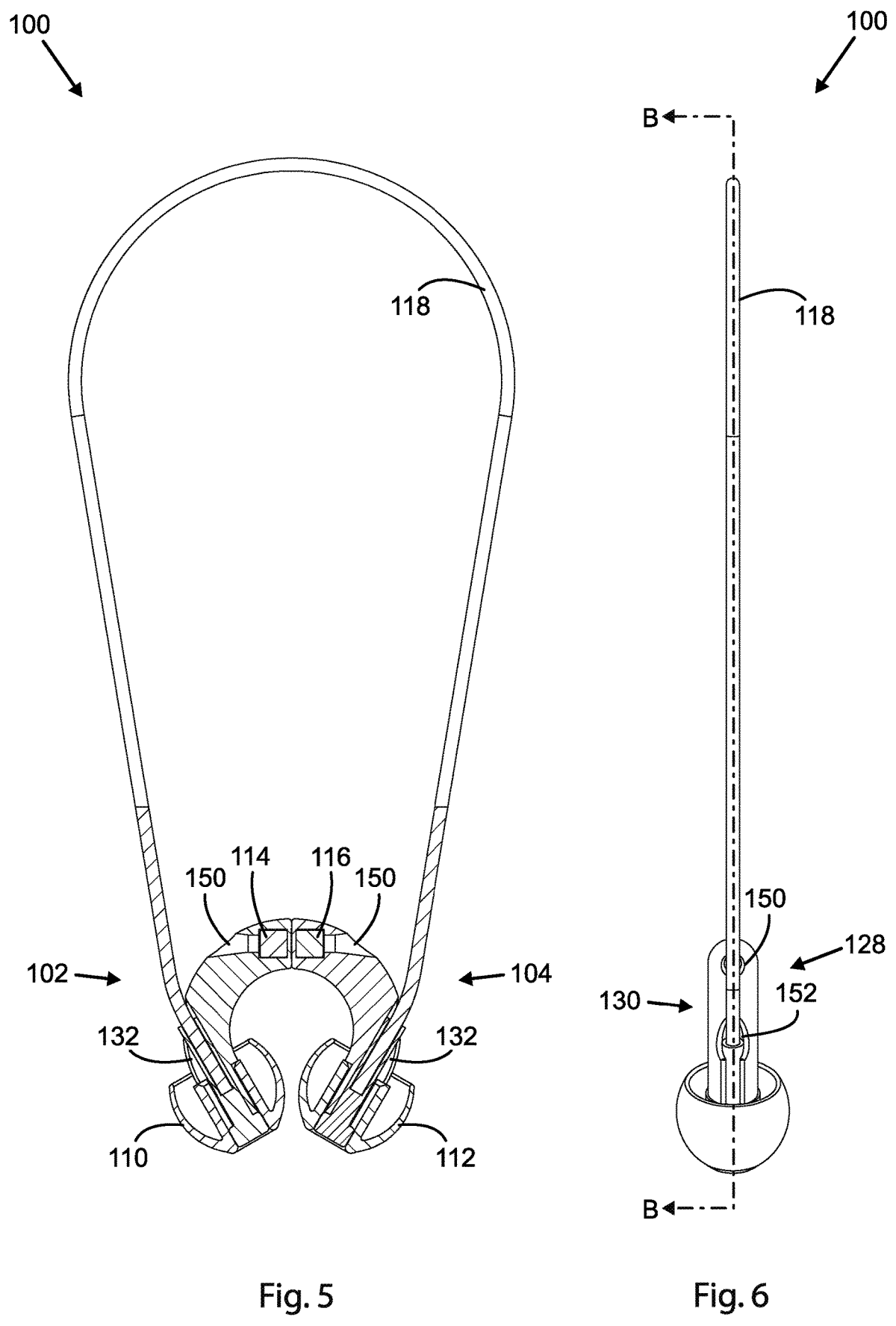

FIG. 5 is a cross-sectional view of the earplug system of FIG. 4, the cross-section being taken along the line B-B of FIG. 6.

FIG. 6 is a side elevational view of the earplug system of FIG. 4.

FIG. 9 is an exploded plan view of a third embodiment of an earplug system, made in accordance with principles of this disclosure.

DETAILED DESCRIPTION

FIGS. 1-16 show various embodiments of an earplug system having a pair of earplugs being selectively connectable (coupled) to each other to form a pendant that can be worn around the neck of a user. Common parts will use common reference numbers.

FIGS. 1-3, 14-16

Figure 1:
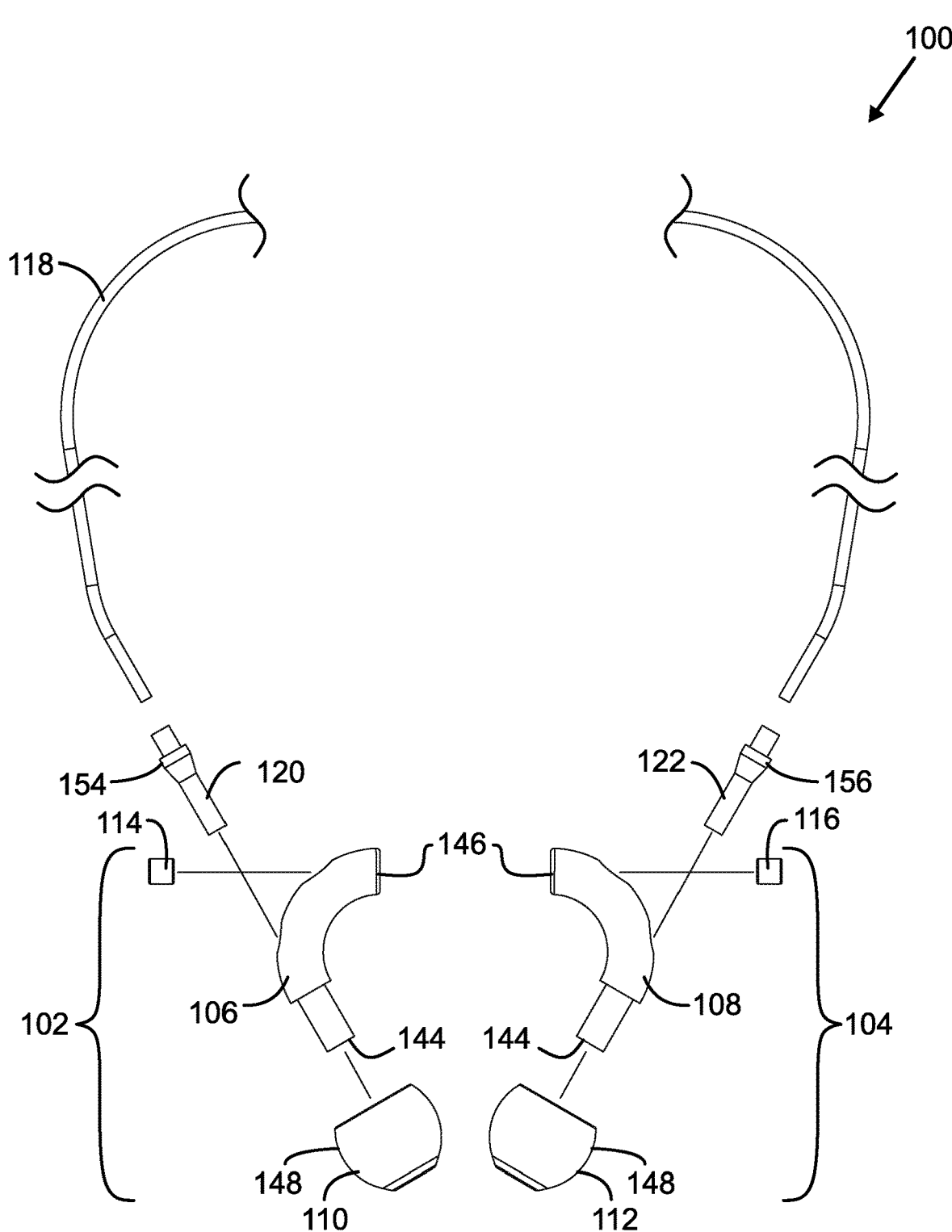
FIG. 1 is an exploded plan view of a first embodiment of an earplug system, made in accordance with principles of this disclosure.

A first embodiment of an earplug system 100 is shown in FIGS. 1-3. The earplug system 100 has a pair of earplugs 102, 104. Each of the earplugs 102, 104 is constructed and arranged to protect hearing by reducing a volume of external noise for the human, when inserted into ears of the human.

Each earplug 102, 104 includes a body portion. The first earplug 102 includes a first earplug body 106, and the second earplug 104 includes a second earplug body 108. Each earplug body 106, 108 is preferably constructed from a soft, compliant material such as silicone or urethane rubber. The earplug bodies 106, 108 are shaped and dimensioned to provide a comfortable fit when inserted into a user's ear while maintaining the structural integrity necessary for proper function. In the example illustrated, the bodies 106, 108 are curved between a tip end 144 and a free end 146. The tip end 144 holds a tip piece 148, which is inserted into the user's ear.

The first earplug body 106 includes a magnet pocket 107 (FIG. 2) that holds a first magnet 114. Similarly, the second earplug body 108 includes a magnet pocket 109 that holds a second magnet 116. The first magnet 114 and the second magnet 116 are oriented with opposing poles facing each other, enabling the earplugs 102, 104 to be selectively coupled and uncoupled from each other.

The magnets 114, 116 are preferably comprised of neodymium and may be embedded or insert-molded into the respective earplug bodies 106, 108. The magnet pockets 107, 109 are illustrated as blind bores, closed at the respective free end 146 of each body 106, 108. The bodies 106, 108 each has an opening 150 (FIG. 2) providing access to the magnet pockets 107, 109.

The earplug bodies 106, 108 are shaped such that when magnetically coupled together, the bodies 106, 108 form a pendant 126 having opposite front and rear surfaces 128, 130 (FIG. 3) each being contained within parallel planes. The front and rear surfaces 128, 130 being within parallel planes allows the pendant 126 to lie flat against the user's chest. The pendant 126 is eye-catching and attractive, and can be embodied in many different configurations. In some cases, the pendant 126 can also be distinctive and source-indicative. In the example shown, the pendant 126 forms, generally, an arc of a toroidal ring that extends between about 250-300°

The tip piece 148 of the first earplug 102 includes a first earplug tip 110 that is removably attached to the first earplug body 106 at the tip end 144. The tip piece 148 of the second earplug 104 includes a second earplug tip 112 that is removably attached to the second earplug body 108 at the tip send 144. Each earplug tip 110, 112 is constructed and arranged to be insertable into a human ear for noise reduction purposes.

The earplug tips 110, 112 are preferably constructed from rubber or foam material. The earplug bodies 106, 108 optionally have, adjacent to the tips ends 144,148, a plurality of ribs 124 (FIGS. 14-16) to enhance friction with the respective tips 110, 112 to provide secure attachment. The ribs 124 are circumferential along the bodies 106, 108 and are axially spaced from each other. In the example embodiment shown, there are two ribs 124 on each body 106, 108 adjacent to the tip ends 144 (i.e., the terminal ends that receive the tips 110, 112 for insertion in an ear). The removable attachment allows the tips 110, 112 to be replaceable or interchangeable based on sizing, user preference, or hygiene requirements.

The earplug system 100 further includes a cord 118 extending between the earplugs 102, 104. The cord 118 typically has a length between the earplugs sufficiently long so that it can be worn around the neck of a human. This length is typically at least 14 inches, but can vary between 12 inches and 36 inches, for example. The cord 118 may comprise tubing, filament, or braided fiber.

Each earplug body 106, 108 includes a cord-receiving cavity 111 (FIG. 2) for attachment to the cord 118. The cord-receiving cavity 111 extends from an aperture 152 in each body 106, 108 in a direction toward the tip end 144. In FIG. 3, it can be seen that the opening 150 and the aperture 152 are circumferentially spaced from each other along the outer radius of each of the bodies 106, 108.

The cord 118 includes a first cord end construction 120 attached to the first earplug body 106 and a second cord end construction 122 attached to the second earplug body 108. Each cord end construction 120, 122 is preferably formed of rigid plastic and is designed to be received within the cord-receiving cavity 111 of the respective earplug body 106, 108. The cord end constructions 120, 122, in this embodiment, are non-removably attached to the respective earplug bodies 106, 108. In other embodiments (described below), the cord 118 is removably attached to the earplug bodies 106, 108.

The non-removably attachment of the cord 118 to each of the bodies 106, 108 can be implemented in a variety of ways. In the example shown in FIGS. 1 and 2, the cord end constructions 120, 122 each has a flared projection 154, 156, which allows the cord end constructions 120, 122 to be inserted into the cord-receiving cavity 111. The cord-receiving cavity 111 can have two regions of inner diameter, such that the cord end constructions 120, 122 are locked into place by engagement between the projection 154, 156 and the transition between the two diameter regions. See FIG. 2. Other methods for non-removable connection are possible.

This configuration allows the earplug system 100 to function both as hearing protection when the tips 110, 112 are inserted into the user's ears, and as an aesthetically pleasing pendant when the earplug bodies 106, 108 are magnetically coupled together and worn around the user's neck via the cord 118

In use, the user will be wearing the earplugs 102, 104 as normal, in the ears, to protect hearing. After the hearing protection is no longer needed, the user removes the first earplug 102 and second earplug 104 from their respective ears. The first tip 110 and second tip 112 are removably attached to their respective earplug bodies 106, 108, and the cord 118 secures the earplugs 102, 104 to each other at opposite ends via the first cord end construction 120 and second cord end construction 122

The user magnetically couples the first earplug 102 and second earplug 104 to each other by bringing the first earplug body 106 and second earplug body 108 together at the respective free ends 146. This allows the first magnet 114 and second magnet 116 to attract and secure the earplugs 102, 104 together, thereby forming pendant 126.

The pendant 126 has opposite front and rear surfaces 128, 130 each being contained within parallel planes. The user then allows the pendant 126 to hang from their neck, with the cord 118 extending around the neck of the user.

FIGS. 4-8

The earplug system 100 of FIGS. 4-8 shows another embodiment. In this embodiment, each one of the cord end constructions 120, 122 is removably attached to a respective one of the earplug bodies 106, 108 in the cord-receiving cavity 111. In addition, the earplugs 102, 104 have an indexing system to ensure proper magnetic alignment between them.

Figure 4:
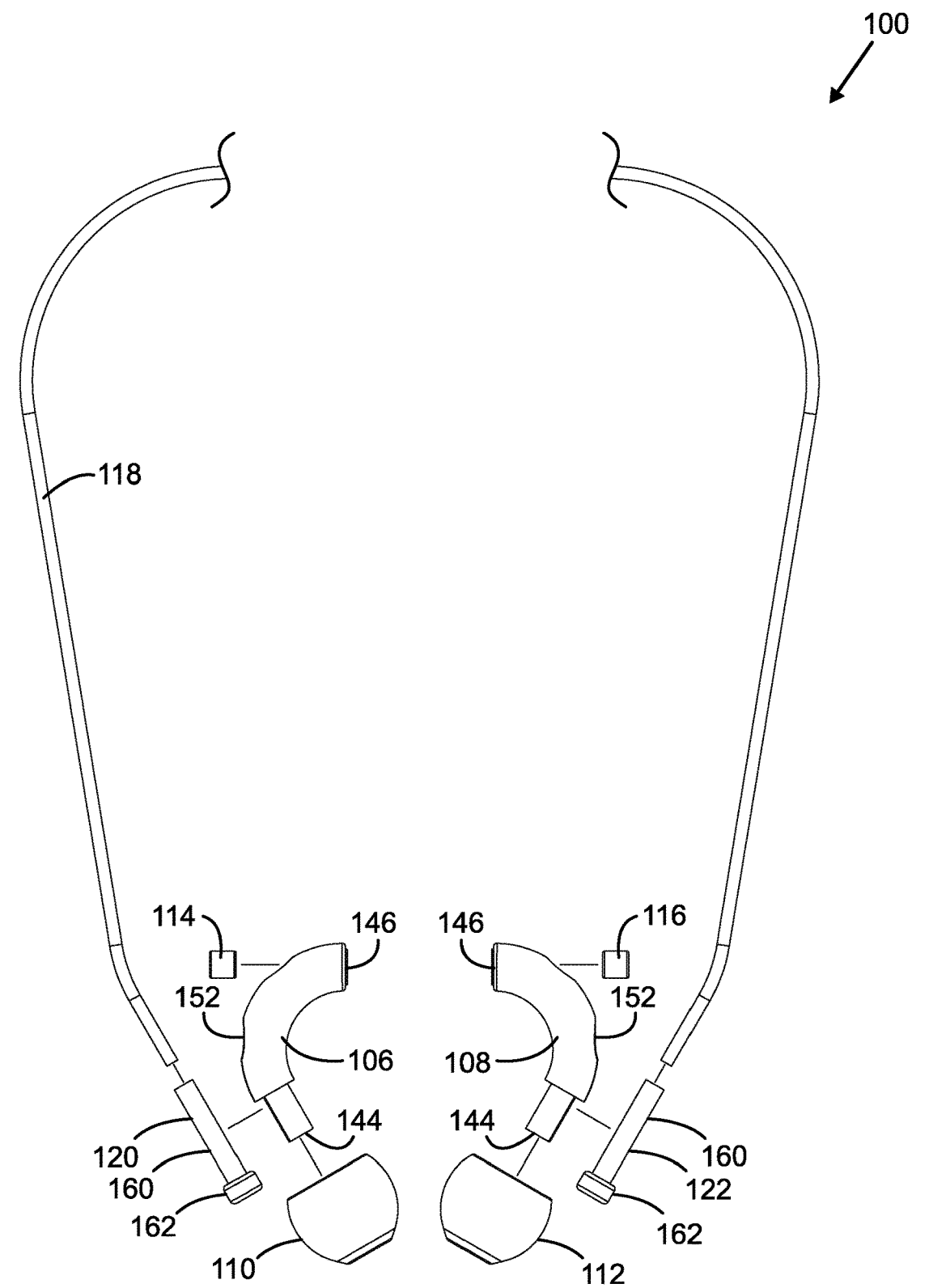
FIG. 4 is an exploded plan view of a second embodiment of an earplug system, made in accordance with principles of this disclosure.

Each earplug body 106, 108 includes a cord slot 132 accessible via aperture 152 in communication with the cord-receiving cavity 111. This cord slot 132 enables the removable attachment of cord end constructions 120, 122 to their respective earplug bodies 106, 108, allowing for interchangeable cord systems. Cords 118 can be changed out based on appearance, including color, texture, etc. Referring to FIG. 4, the cord end constructions 120, 122, in this embodiment, have cylindrical bodies 160 with increased diameter end caps 162, which are received through the aperture 152 and in the cord slot 132. There is a tight, interference fit between the end caps 162 and the cord-receiving cavity 111 to hold the cord end constructions 120, 122 (and thereby the cord 118) in place within the earplug bodies 106, 108. The cord end constructions 120, 122 can be removed (without damage to the cord end constructions 120, 122, the cord 118, or the earplug bodies 106, 108) by pulling the cord 118 while holding the earplug bodies 106, 108.

Figure 8:
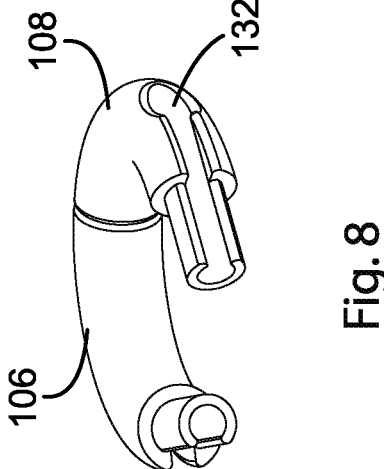
FIG. 8 is a perspective view of each body of the earplug system of FIG. 4 in a coupled position.
Figure 7:
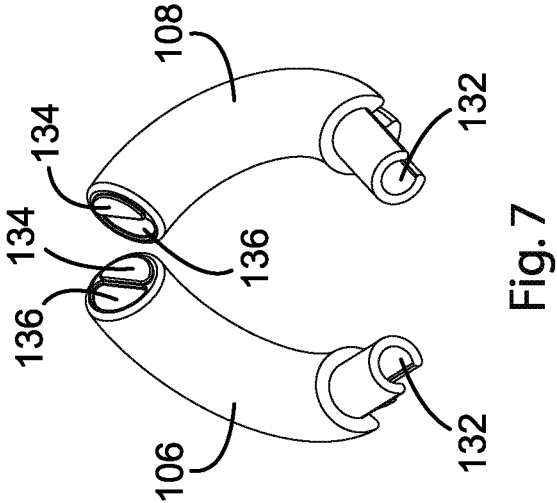
FIG. 7 is a perspective view of each body of the earplug system of FIG. 4 in an uncoupled position.
Figures 10, 11, 12, 13:
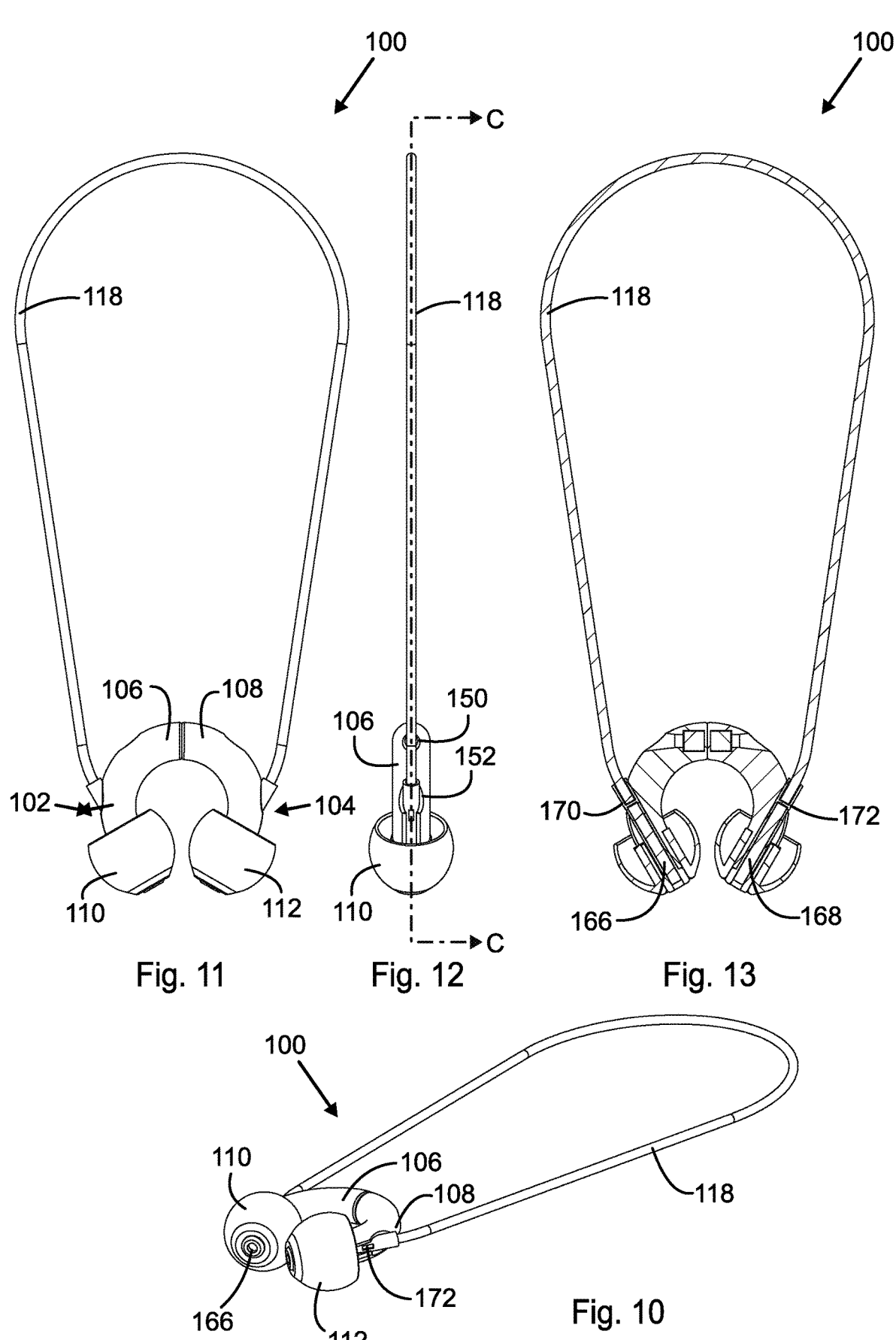
FIG. 10 is a perspective view of the earplug system of FIG. 9.
FIG. 11 is a plan view of the earplug system of FIG. 9.
FIG. 12 is a side elevational view of the earplug system of FIG. 9.
FIG. 13 is a cross-sectional view of the earplug system of FIG. 9, the cross-section being taken along the line C-C of FIG. 12.
Figure 16:
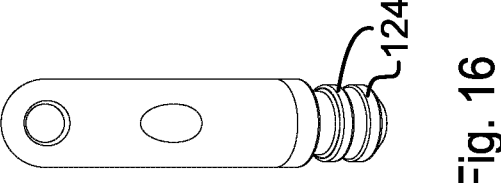
FIG. 16 is a side elevational view of each body of the earplugs of FIG. 14.
Figure 14:
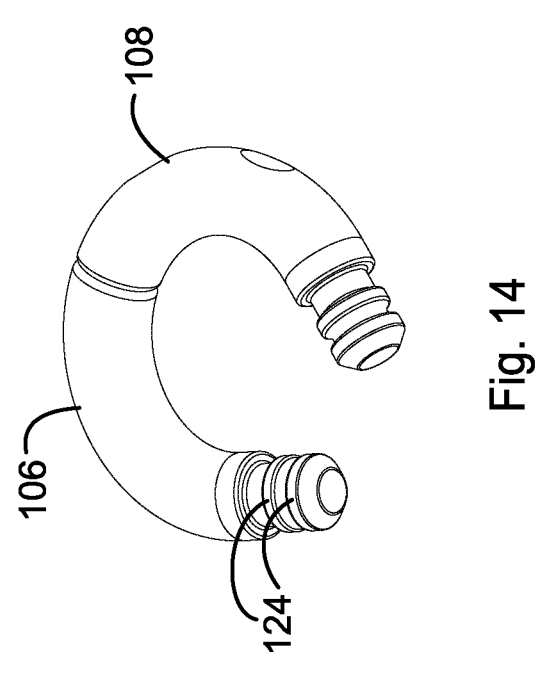
FIG. 14 is a perspective view of an alternative embodiment of each body of the earplugs of FIG. 1 in a coupled position.

In reference now to FIG. 7, each earplug body 106, 108 incorporates an indexing system featuring an indexing protrusion 134 and an indexing recess 136. The protrusion 134 of the first earplug body 106 is received within the recess 136 of the second earplug body 108; and the protrusion 134 of the second earplug body 108 is received within the recess 136 of the first earplug body 106. This indexing protrusion 134 and recess 136 arrangement assists with proper alignment between the magnets 114, 116 when the earplugs 102, 104 are magnetically coupled together (FIG. 8). The ensures proper orientation and flat plane alignment when the earplugs 102, 104 are magnetically coupled, such that the opposite front and rear surfaces 128, 130 (FIG. 6) are contained within parallel planes to each other.

Figure 15:
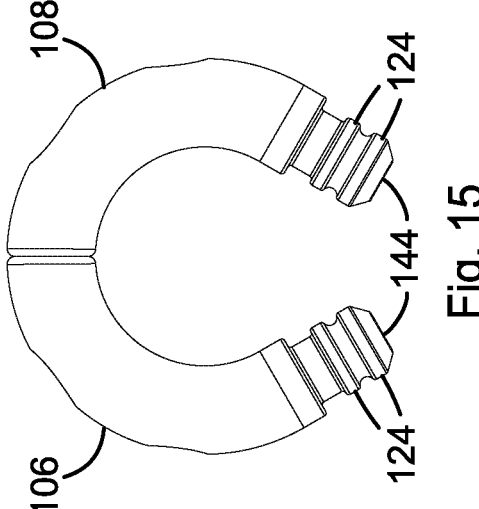
FIG. 15 is a plan view of the earplugs of FIG. 14.

In the example shown in FIG. 15, each earplug body 106, 108 may include an optional plurality of ribs 124 to enhance friction with the respective earplug tips 110, 112. These ribs 124 are circumferential along the bodies 106, 108 and axially spaced from each other, providing secure removable attachment.

The system 100 of FIGS. 4-8 can be used as described above in the first embodiment. In addition, in this embodiment, the removal step can include pulling on cord 118 to remove tips 110, 112 of each earplug from the ears.

The magnetic coupling step may include inserting indexing protrusion 134 from the first earplug 102 into indexing recess 136 of the second earplug 104, and inserting second indexing protrusion 134 from the second earplug 104 into the corresponding recess 136 of the first earplug 102. This ensures proper alignment when forming the pendant 126.

The method further includes removing cord 118 from the earplugs 102, 104 via cord slot 132. This is done by pulling the cord 118 to pull the cord end constructions 120, 122 out of the earplug bodies 106, 108. Next, the user provides a different cord 118 and removably attaches it to the earplug bodies 106, 108 through the cord slots 136.

FIGS. 9-13

The earplug system 100 of FIGS. 9-13 shows another embodiment. In this embodiment, there is a passive acoustic sound filter 166, 168 in each earplug 102, 104, which can be tuned to attenuate specific frequencies. The sound filter may be composed of sound-absorbing fibers, selected for their ability to attenuate specific frequencies. Material can be selected to attenuate specific sound frequencies. The density and material of the fiber filter can be tuned to achieve various levels of sound blocking or frequency-specific damping.

The filters 166, 168 may be incorporated into the earplugs 102, 104 in a variety of locations. In the example shown in FIGS. 9-13, the filters 166, 168 are held by the cord end constructions 120, 122. The cord end constructions 120, 122 each includes an aperture arrangement 170, 172, respectively, to allow ambient sound to enter and pass through the filter 166, 168 and then into the ear canal.

As can be seen in FIG. 9, opposite ends 174, 176 of the cord 118 are received in one end of the cord end constructions 120, 122, while the filters 166, 168 are received in the opposite end (the end that is within the tips 110, 112) of the cord end constructions 120, 122. The cord end constructions 120, 122 are positioned within the earplug bodies 106, 108, such that the aperture arrangements 170, 172 are external to the earplug bodies 106, 108 and openly exposed to ambient sound.

In this embodiment, the cord 118 is removably mounted to the earplug bodies 106, 108. In other arrangements, the cord 118 can be non-removably mounted to the earplug bodies 106, 108, such as shown in FIG. 1.

The system 100 of FIGS. 9-13 can be used as described above in the first and second embodiments. In addition, the method can include, before the step of removing the earplug 102, 104, from each ear of a user, filtering out sound using passive acoustic filter 166, 168 in each earplug 102, 104.

The above describes example principles. Many embodiments can be made using these principles.

What is claimed is:

1. An earplug system for a human, comprising:
(a) a pair of earplugs; each of the earplugs being constructed and arranged to reduce volume of external noise for the human, when inserted into ears of the human;
(b) a pair of magnets of oriented with opposing poles facing each other; each of the magnets embedded within by one of the earplugs to permit the earplugs to be selectively coupled and uncoupled from each other; and
(c) a cord extending between the earplugs; the cord having a length between the earplugs of at least 14 inches.

2. The earplug system of claim 1, wherein each of the earplugs includes:
(a) a body holding one of the magnets and being attached to the cord; and
(b) a tip constructed and arranged to be insertable into the human ear;
(i) the tip comprising rubber or foam;
(ii) the tip being removably attached to the body.

3. The earplug system of claim 2, wherein the cord includes:

(a) a pair of cord end constructions on opposite ends of the cord;

(b) each cord end construction being attached to the body of one of the earplugs.

4. The earplug system of claim 3, wherein each body includes:

(a) a magnet pocket holding one of the magnets; and (b) a cord-receiving cavity.

5. The earplug system of claim 4 wherein each one of the cord end constructions is non-removably attached to a respective one of the earplug bodies in the cord-receiving cavity.

6. The earplug system of claim 4 wherein each one of the cord end constructions is removably attached to a respective one of the earplug bodies in the cord-receiving cavity.

7. The earplug system of claim 6, wherein each body includes a cord slot in communication with the cord-receiving cavity.

8. The earplug system of claim 3, further including a pair of passive acoustic filters for each earplug.

9. The earplug system of claim 8, wherein each of the passive acoustic filters is held by a respective one of the cord end constructions.

10. The earplug system of claim 3, wherein:

(a) each body comprises silicone or urethane rubber;

(b) each of the magnets comprises neodymium embedded or insert-molded into one of the bodies;

(c) each cord end construction comprises rigid plastic; and (d) each cord comprises one of tubing, filament, or braided fiber.

11. The earplug system of claim 2, wherein each body includes an indexing protrusion and recess arrangement to assist with alignment between the magnets.

12. The earplug system of claim 2, wherein each body includes a plurality of ribs to enhance friction with one of the tips.

13. The earplug system of claim 2, wherein each body is shaped such that when magnetically coupled together, the bodies form a pendant; the pendant having opposite front and rear surfaces each being contained within parallel planes.

14. A method of using an earplug system; the method comprising:

(a) removing an earplug from each ear of a user; each earplug being constructed and arranged to reduce volume of external noise; each earplug having a body embedding a magnet; a tip removably attached to the body; and a cord secured to the body and securing the earplugs to each other at opposite ends of the cord;

(b) magnetically coupling the earplugs to each other to form a pendant; and (c) allowing the pendant to hang from a neck of the user, with the cord extending around the neck of the user.

15. The method of claim 14, wherein the step of removing the earplug from each ear includes pulling on the cord to remove the tip of each earplug from one of the ears.

16. The method of claim 14, wherein the step of magnetically coupling the earplugs includes inserting a first projection from a first of the earplugs into a second recess of a second of the earplugs; and inserting a second projection from the second of the earplugs into a first recess of the first earplug.

17. The method of claim 14, wherein the step of magnetically coupling the earplugs includes the pendant having opposite front and rear surfaces each being contained within parallel planes.

18. The method of claim 14, further including:

(a) removing the cord from the earplugs; and (b) providing a different cord and removably attaching the different cord to the bodies of the earplugs.

19. The method of claim 14, further including before the step of removing the earplug from each ear of a user, filtering out sound using a passive acoustic filter in each earplug.

\* \* \* \* \*